US007483838B1

(12) United States Patent
Marks (10) Patent No.: US 7,483,838 B1
(45) Date of Patent: Jan. 27, 2009

(54) SYSTEM AND METHOD FOR RECRUITMENT OF CANDIDATES FOR CLINICAL TRIALS WHILE MAINTAINING SECURITY

(75) Inventor: James D. Marks, 101 W. 79th St., New York, NY (US) 10024

(73) Assignee: James D. Marks, New York, NY (US)

(*) Notice: Subject to any disclaimer, the term of this patent is extended or adjusted under 35 U.S.C. 154(b) by 0 days.

(21) Appl. No.: 09/556,945

(22) Filed: Apr. 21, 2000

(51) Int. Cl.
*G06Q 10/00* (2006.01)
(52) U.S. Cl. .............................................. 705/2; 705/3
(58) Field of Classification Search .................. 705/2–3; 434/322
See application file for complete search history.

(56) References Cited

U.S. PATENT DOCUMENTS

| | | | | |
|---|---|---|---|---|
| 5,758,324 | A | 5/1998 | Hartman et al. ................. | 705/1 |
| 5,978,768 | A | 11/1999 | McGovern et al. .............. | 705/1 |
| 5,991,731 | A * | 11/1999 | Colon et al. .................... | 705/3 |
| 6,149,440 | A | 11/2000 | Clark et al. ................. | 434/322 |
| 6,151,581 | A * | 11/2000 | Kraftson et al. ................ | 705/3 |
| 6,171,112 | B1 * | 1/2001 | Clark et al. ..................... | 434/322 |
| 6,272,470 | B1 * | 8/2001 | Teshima .......................... | 705/3 |
| 2002/0002474 | A1 * | 1/2002 | Michelson et al. .............. | 705/3 |

OTHER PUBLICATIONS

PR Newswire, New York, Jun. 28, 1999; drkoop.com & Quintiles Launch Service to Recruit Clinical Trial Patient on the Interne p. 1.*
Sharon Machlis, Oct. 14, 1998; "Web links cancer patient to drug trials", Computerworld, p. 1-3.*
Gary Baldwin, Nov. 16, 1998; "System makes it easier to link patient to clinical trials", Americal Medical News, vol. 41, Iss. 43, p. 25, 2 pgs.*
Business Editors, Jan. 26, 1999; "Object Products, Inc. to Demonstrate Clinical Trials Patients Recruitment Solution at HIMSS", Business Wire, p. 1.*
PR Newswire, Jan. 6, 1999; "CenterWatch Launches Services to Help Patient Access NIH Clinical Trials", p. 1.*
PR Newswire, Apr. 13, 1999, GO Network™ and drkoop.com Strike Exclusive $57 Million Cross-Network Partnership, p. 1.*
PR Newswire, New York, Jun. 28, 1999; drkoop.com & Quintiles Lauch Service to Recruit Clinical Trial Patient on the Internet p. 1, 3 pages.*
www.koop.com.
www.americasdoctor.com.
www.acurian.com.

* cited by examiner

*Primary Examiner*—Robert W Morgan
(74) *Attorney, Agent, or Firm*—Darby & Darby P.C.

(57) ABSTRACT

An on-line click wrap electronic agreement that a user must agree to prior to being registered as a volunteer and considered as a potential candidate in a clinical trial or research study. The agreement authorizes the release of the end user's medical and/or personal information to representatives of the clinical trials and research studies for which the volunteer may be considered as a potential candidate. After receiving the end user's consent to the click wrap agreement an electronic survey form is generated by a secure server and displayed at the end user's computer terminal. Responses by the end user to the survey form are kept secure as much as possible while being transmitted from the computer terminal across the network to the server and while stored and accessed only by authorized personnel at the central office.

17 Claims, 9 Drawing Sheets

Health Survey

1. How old are you? ☐ years old

2. Please enter your sex:
   ○ I am male
   ○ I am female

3. How would you characterize you health?

○ excellent
   ○ good
   ○ fair
   ○ poor

4. How long do you think you have been infected? (Note: The Health Survey focuses on people who are HIV-postive.)

○ less than one year
   ○ one to two years
   ○ two to four years
   ○ four to six years
   ○ six to eight years
   ○ more than 11 years
   ○ I don't know 5. Would you be willing to particpate as a subject in a medical research project?

○ yes
   ○ no 6. what was your last viral load count?
   ☐
   ○ I don't know

FIG. 3A

7. What was your last T-Cell count?
○ under 100
○ 100 to 200
○ 200 to 300
○ 300 to 400
○ 400 to 500
○ 500 to 600
○ over 600
○ I don't know 8. Which HIV antiviral medications are you currently taking? Select as many as apply:

☐ 3TC (Lamivudine)
☐ Abacavir (Ziagen, formerly 1592U89)
☐ Ampernavir (Agenerase)
☐ AZT (Zidovudine, ZDV)
☐ Combivir (AZT plus 3TC)
☐ d4t (Stavudine)
☐ ddC (Hivid)
☐ ddI (Didanosine)
☐ Delavirdine (Rescriptor)
☐ Efavirenz (Sustiva, formerly DMP-266)
☐ Loviride
☐ Nevirapine (Vramune)
☐ Indinavir (Crixivan, MK-639)
☐ Nelfinavir (Viracept)
☐ Ritonavir (Norvir)
☐ Saquinavir (Invirase, Fortovase)
☐ Other anti-HIV medications (please specify; note that more medications are listed in Question 10)

☐ I don't know
☐ I am currently not taking any medications

FIG. 3B

9. Which HIV antiviral medications have you taken in the past? Select as many as apply:

☐ 3TC ( Lamivudine)
☐ Abacavir (Ziagen, formerly 1592U89)
☐ Ampernavir (Agenerase)
☐ AZT (Zidovudine, ZDV)
☐ Combivir (AZT plus 3TC)
☐ d4t (Stavudine)
☐ ddC (Hivid)
☐ ddI (Didanosine)
☐ Delavirdine (Rescriptor)
☐ Efavirenz (Sustiva, formerly DMP-266)
☐ Loviride
☐ Nevirapine (Viramune)
☐ Indinavir (Crixivan, MK-639)
☐ Nelfinavir (Viracept)
☐ Ritonavir (Norvir)
☐ Saquinavir (Invirase, Fortovase)
☐ Other (please specify)

☐ I don't know
☐ I have never taken any medications for HIV

10. Which HIV antiviral medications have you taken in the past? Select as many as apply:
☐ Acyclovir (Zovirax)
☐ Adefovir (Preveon)
☐ Amphotericin B (Fungizone)
☐ Atovaquone (Mepron)
☐ Azithromycin (Zithromax)
☐ Bactrim (TMP/SMX)
☐ Cidofovir (Vistide)
☐ Ciprofloxacin(Cipro)
☐ Clarithromycin (Biaxin)
☐ Clindamycin (Cleocin)
☐ Clofazimine (Lamprene)
☐ Cycloserine (Seromycin)
☐ Dapsone
☐ Emivirine (MKC-442)
☐ Ethambutol
☐ Fluconazole (Diflucan)
☐ Flucytosine (Ancobon)
☐ Fomivirsen (ISIS 2922)
☐ Foscarnet (Foscavir)
☐ Ganciclovir (Cytovene)
☐ Inderal
☐ Isoniazid
☐ Itraconazole (Sporanox)
☐ Leucovorin
☐ Pentamidine (aerosolized)
☐ Prozac
☐ Pyrazinamide
☐ Pyrimethamine (Daraprim, Fansidar)
☐ Rifabuttin (Mycobutin)
☐ Rifampin (Rifadin)
☐ Rimantadine
☐ Sparfloxacin
☐ Sulfadiazine
   Other (please list all other medications you are taking)
   [                              ]
☐ I am not taking any additional medications 11: Have you ever been diagnosed with any of the following infections or complictions? Select as many as apply:

☐ Anemia
☐ Cancer
☐ Candidiasis
☐ Cryptococcosis
☐ Cryptosporidiosis
☐ Cytomegalovirus (CMV)
☐ Hepatitis
☐ Herpes
☐ Kaposi's Sarcoma (KS)
☐ Microsporidiosis
☐ Mycobacterium Avium Complex (MAC)
☐ Neuropathy
☐ AIDS Dementia
☐ PML (Progressive Multifocal Leuloencephalopathy)
☐ Other Neurological/Neurocognitive Complications
☐ Non-Hodgkins Lymphoma
☐ Oral and Esophageal Thrush
☐ Pneumocystis Carinii Pneumonia (PCP)
☐ Sinusitis
☐ Toxoplasmosis
☐ Turberculosis
☐ Wasting
☐ Other (please specify)

☐ I have never been diagnosed with any infection or complication of HIV

12. Can we contact you by e-mail about participating in a clinical research project?

○ No
○ Yes

If yes, please provide you e-mail address:
[          ]

13. May we phone you? (Note: To be contacted to Participate, you must provide an e-mail address or phone number)

○ No
○ Yes

If yes, please provide you phone number:
area code [    ] number [          ]

14. Please provide you name and place of residence>

Last name:
[          ]

First name:
[          ]

Place of residence:

City [          ] State [          ▼] Zip Code [     ]

15. In order for us to identify you properly, please give us you brithdate:

Month [        ] Day [    ] Year: [      ]

Thank you for taking the time to take this survey. Please note that no one will contact you unless or until there is an appropriate request from a lab or researcher.

[ Submit ]

FIG. 4

Please fill in the following form if you'd like to remove your name from our list of volunteers. Please be as accurate as possible so that we will be able to locate you orginal submission.

[____________________] First name

[____________________] Last name

Birthdate:
Month:[________] Day:[____] Year:[______]

[Submit]

SYSTEM AND METHOD FOR RECRUITMENT OF CANDIDATES FOR CLINICAL TRIALS WHILE MAINTAINING SECURITY

BACKGROUND OF THE INVENTION

1. Field of the Invention

The present invention relates generally to a system for recruitment of candidates for clinical trials, and in particular to the recruitment of candidates, such as individuals who are afflicted with AIDS/HIV positive, who require a certain level of privacy concerning access to their personal and medical information. The invention is also directed to a method of using the same.

2. Description of Related Art

Before a drug or medical technique is approved for use on the public at large, it is administered to a limited number of patients who participate in clinical trials. It is necessary when selecting individuals to participate in the clinical trials to choose only those individuals who meet particular exclusion and inclusion criteria for a specific trial. Selection of candidates to participate in such clinical trials may depend on factors, such as the gender, age, symptoms, prognosis, and previous medical treatments.

Conventional methods of solicitation, such as newspaper and magazine advertisements have heretofore been widely used to solicit individuals to participate in clinical trials. By way of example, an advertisement may be directed to individuals who suffer from asthma and are currently on steroids. Individuals who meet the requirements specified in the advertisement are invited to call a particular number or inquire to be considered as a candidate to participate in the clinical trial.

With the advent of the Internet, web sites, such as Koop.com, Americasdoctor.com and Intertrials.com, have electronically implemented the conventional solicitation process for on-line recruitment of candidates for clinical trials. The procedures used by these conventional web sites, however, are not suitable for receiving personally identifiable medical data concerning patients who suffer from diseases, ailments, disorders, and medical conditions, such as HIV/AIDS, that require a certain level of security against potential unwanted dissemination of personal and/or medical information, and the right to remove one's name from a list of volunteers. Not only is the privacy of such data desirable from the point of view of the individual and their family, but legislation and regulations mandate the level of security to be accorded personal and medical information. For example, the federal department of Health and Human Services has recently promulgated regulations concerning the level of security to be accorded transmission of medical records and personal data, and in particular New York legislation requires that prior to dissemination of medical information the individual sign a release form and that an opt out method be available when recruiting candidates for clinical trials. Other countries have recently adopted guidelines, such as the European Union data directive concerning procedural aspects of the dissemination of personal and medical information.

It is therefore desirable to develop a system and method for online recruitment of candidates for clinical trials and research studies that overcomes the aforementioned problems.

SUMMARY OF THE INVENTION

The following terms used to describe the invention are defined as follows:

"End user" is an individual that accesses the web site for on-line recruitment of candidates for clinical trials.

"Volunteer" is an end user that visits and registers with the web site to be considered as a potential candidate for a clinical trial.

"Candidate" is a volunteer selected to take part in a clinical trial.

"Web site" is a server application which accepts connections from client programs, such as browsers, that allow a remote end user to access and register as a volunteer for on-line recruitment of candidates for clinical trials.

The terms "clinical trials" and "research studies" are used interchangeably throughout the description and the claims.

It is an object of the present invention to develop an on-line click wrap agreement for the release of medical and personal information by end users prior to volunteering to be considered as a potential candidate for clinical trials. The agreement authorizes the release of the end user's medical and/or personal information to representatives of the clinical trials and research studies for which the volunteer may be considered as a potential candidate. After receiving the end user's consent to the click wrap agreement an electronic survey form is generated by a secure server and displayed at the end user's computer terminal. Responses by the end user to the survey form are kept secure as much as possible while being transmitted from the computer terminal across the network to the server and while stored and accessed only by authorized personnel at the central office.

The invention is directed to a method for using a system for on-line recruitment of candidates for clinical trials in which an end user's consent to an electronic agreement relating to volunteering as a potential candidate for a clinical trial and the release of at least one of medical and personal information is received by a central office.

In addition, the invention relates to a system for on-line recruitment of candidates for clinical trials over a network including a secure server for generating an electronic agreement, and one or more computer terminals on which is displayed the electronic agreement. The computer terminal is used by an end user to provide their consent to the electronic agreement to volunteer as a potential candidate for a clinical trial and release medical and/or personal data. In this configuration the server and computer terminals are connected via a network.

BRIEF DESCRIPTION OF THE DRAWING

The foregoing and other features of the present invention will be more readily apparent from the following detailed description and drawings of illustrative embodiments of the invention wherein like reference numbers refer to similar elements throughout the several views and in which.

DETAILED DESCRIPTION OF THE INVENTION

By way of example, the discussion of the system and method in accordance with the present invention is directed to on-line recruitment of volunteers as potential candidates for clinical trials relating to drugs and/or medical treatment of individuals suffering from AIDS/HIV. It should be noted, however, that the recruitment is also applicable to other diseases, ailments, disorders, and medical conditions, such as infectious diseases, or infertility, in which individuals suffering therefrom are stigmatized and thus, would benefit from the implementation of optimum security measures. In addition, the system is also advantageous in view of recent federal and state laws and regulations that mandate the level of security to be accorded the transmission and dissemination of personal and medical data.

Figure 1:
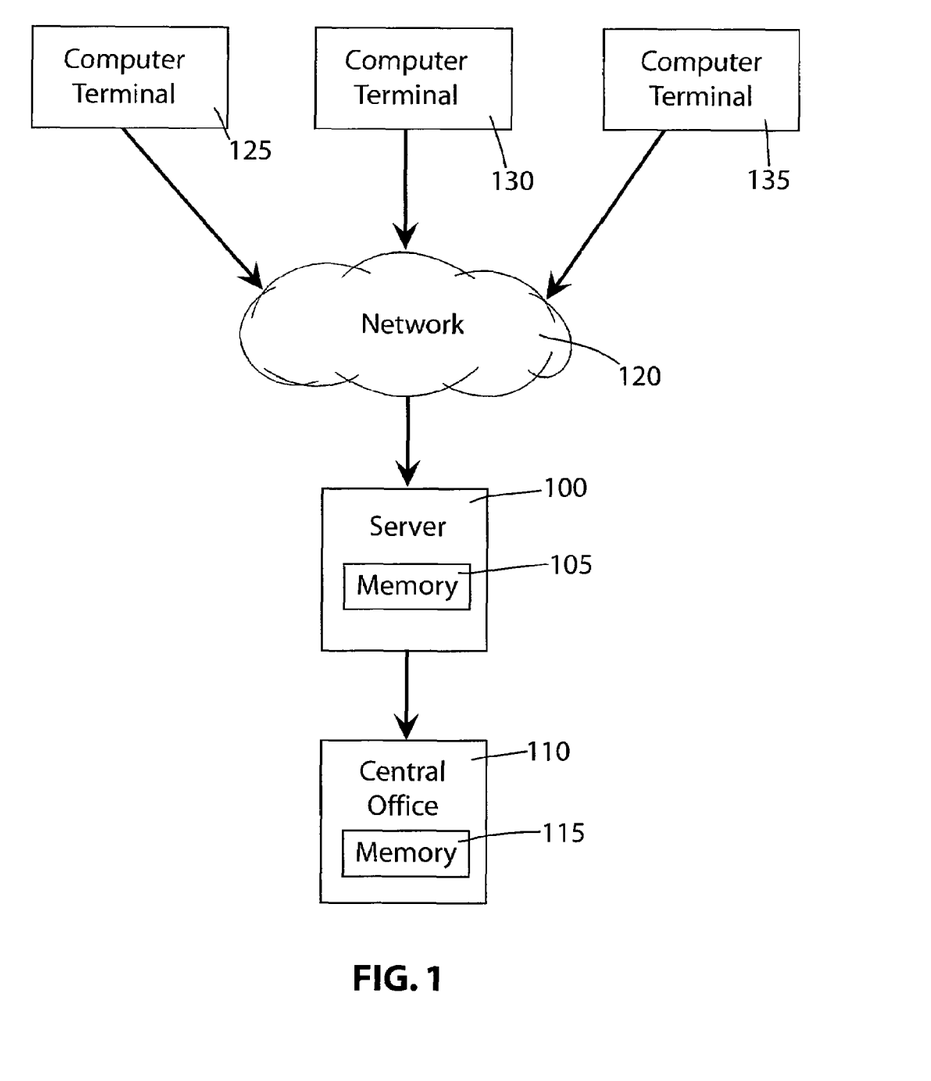
FIG. 1 is an exemplary high-level diagram of a secure system for on-line recruitment of candidates for clinical trials in accordance with the present invention.

FIG. 1 is a high-level diagram of a system or server 100 having a memory device 105. System 100 is connected to a central or main office 110 having a memory device 115. Although the main office 110 is shown in FIG. 1 as separate and remote from the system 100, the two devices may be in a single location or unit. System 100 is accessed by multiple computer terminals 125, 130, 135 connected via a network 120, such as the Internet. While the system and method in accordance with the present invention is described in the context of the Internet or world wide web, it can also be used in other network environments, such as a local area network (LAN), Intranet, wide area network (WAN), or various wireless technology platforms, where the system and software are accessible by both subscribers and end users alike from remote locations. Only three computer terminals are shown, however, any number of computers may be connected to network 120 through known communication interfaces, such as an external or built-in modem (not shown). End users may access the system from any computer terminal throughout the world having appropriate network Internet access and software, such as a web browser. The system 100 uses a secure server, such as Netscape™, using secure socket layer (SSL) protocols or alternative security means. System 100 may be designed so that an end user must employ a web browser that supports SSL. In a preferred embodiment, system 100 notifies the end user if their web browser does not support SSL or if the particular version of the Internet access software installed by the end user falls below a minimum acceptable level of security functionality.

Figure 2:
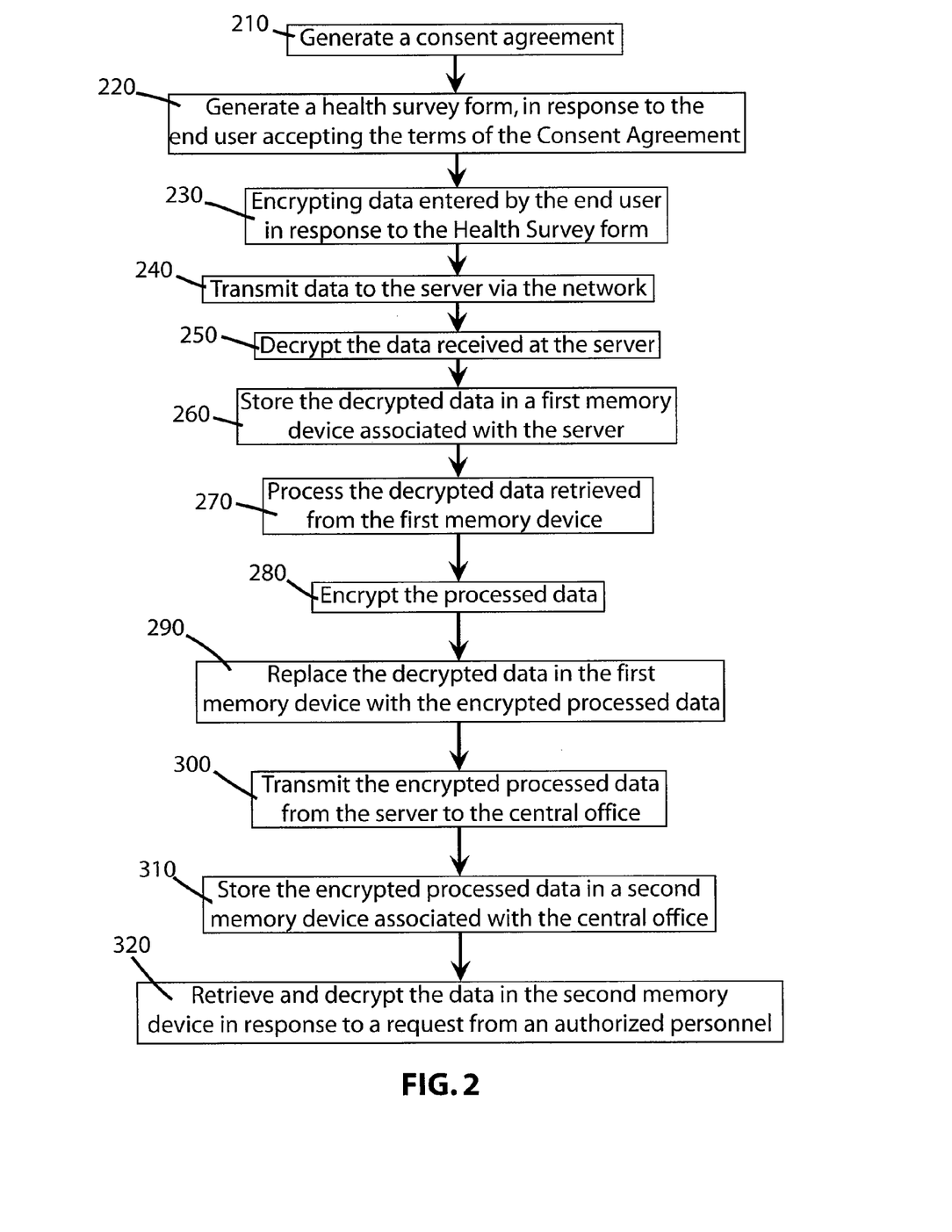
FIG. 2 is an exemplary flow chart of the operating steps of the secure system for on-line recruitment of candidates for clinical trials in accordance with the present invention.
Figure 3A:
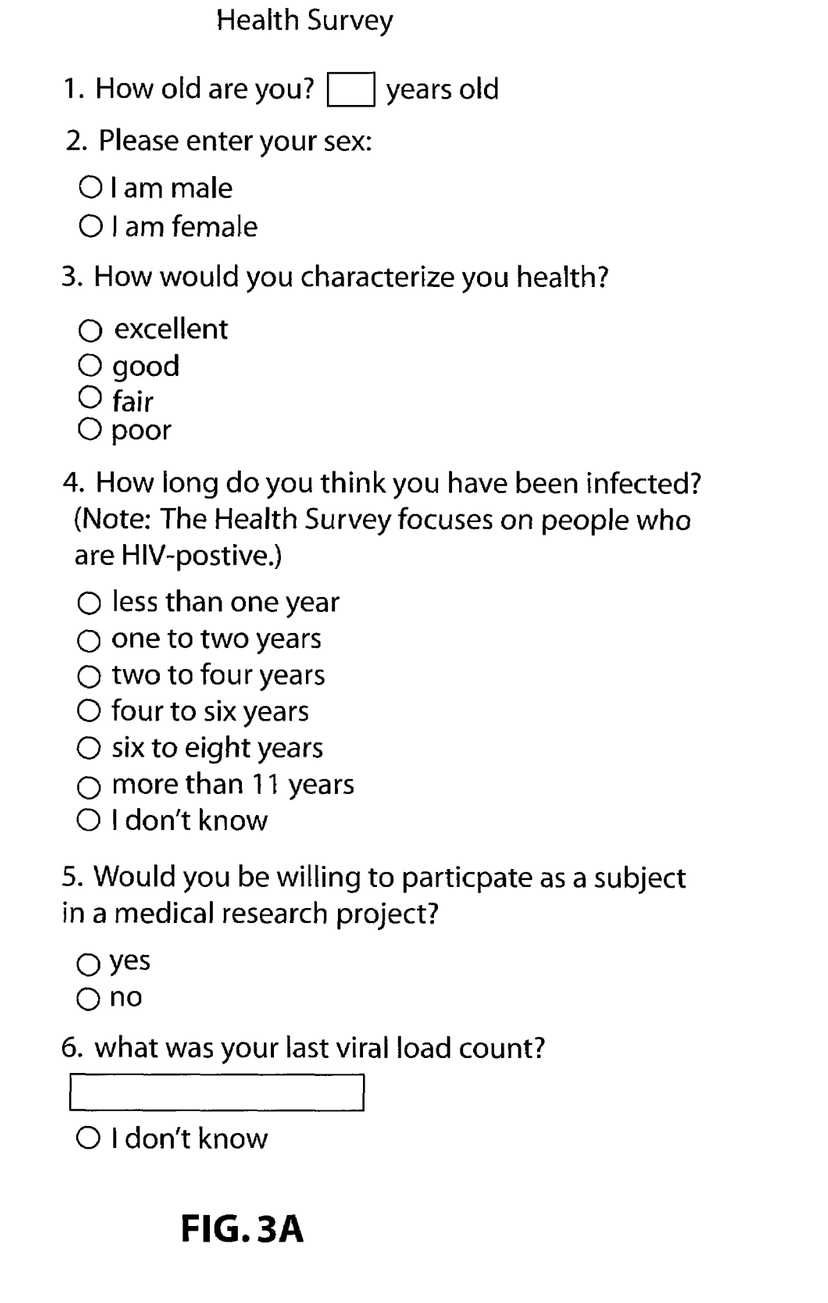
FIGS. 3a-3f is an exemplary Health Survey form display screen in accordance with the present invention.
Figure 3B:
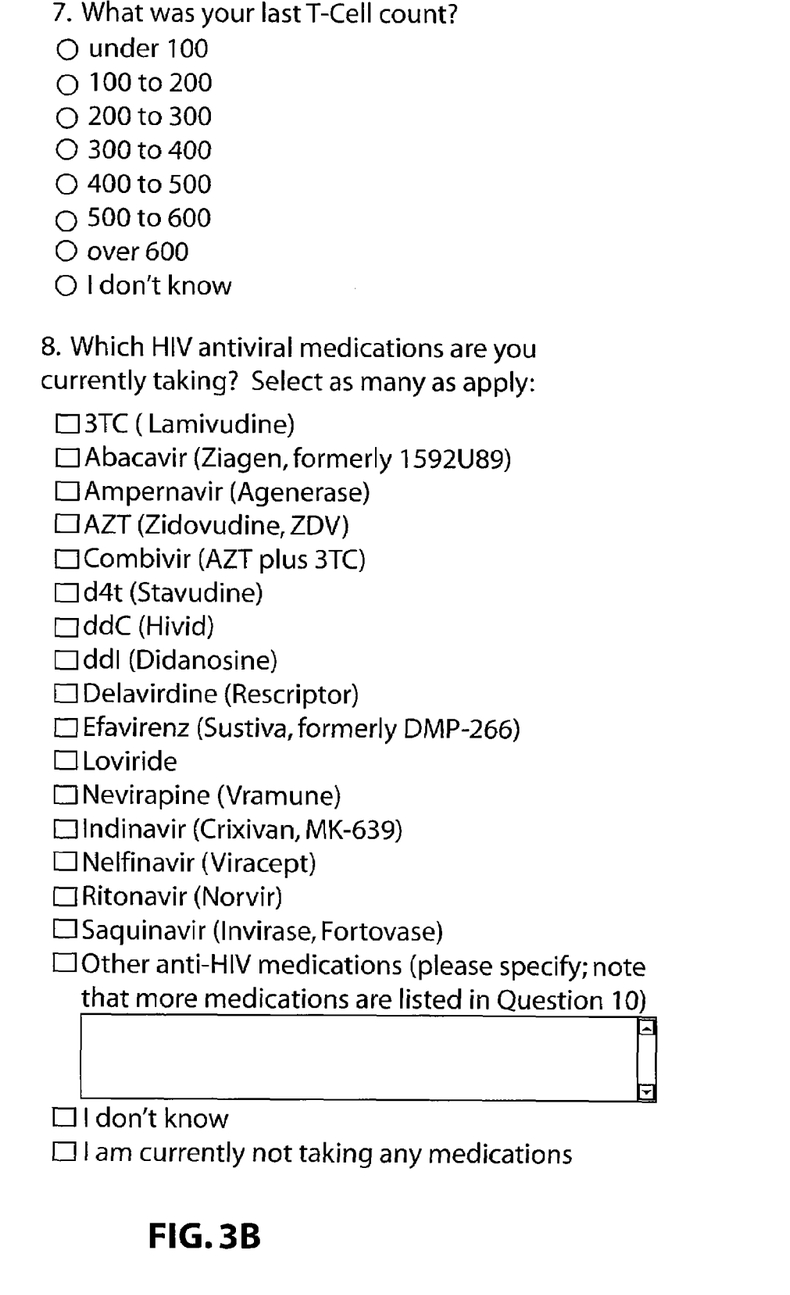
Figure 3C:
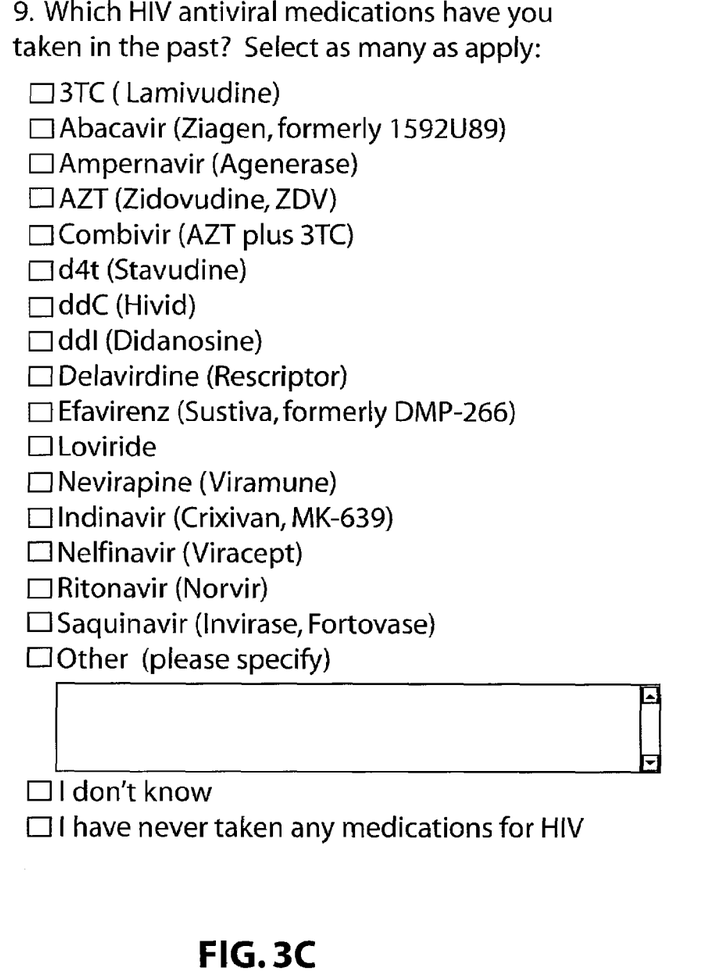
Figure 3D:
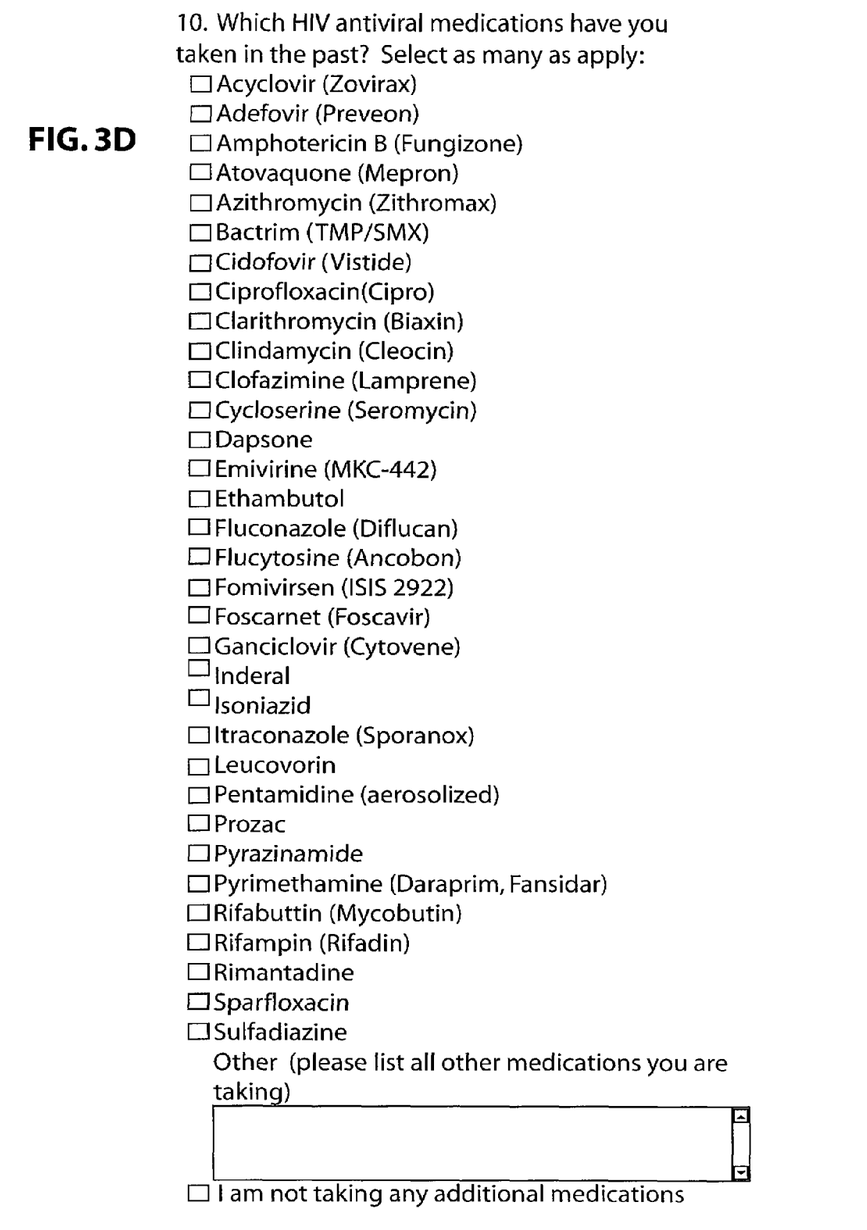
Figure 3E:
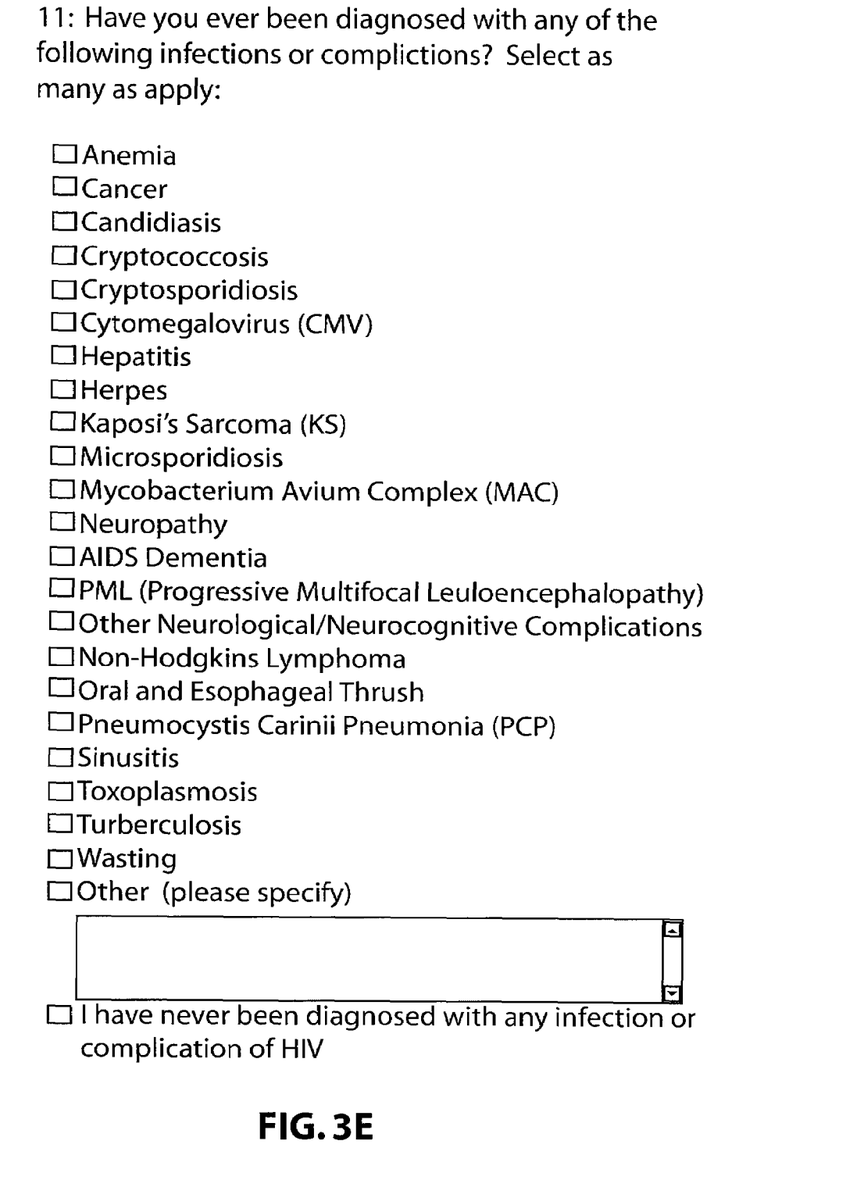
Figure 3F:
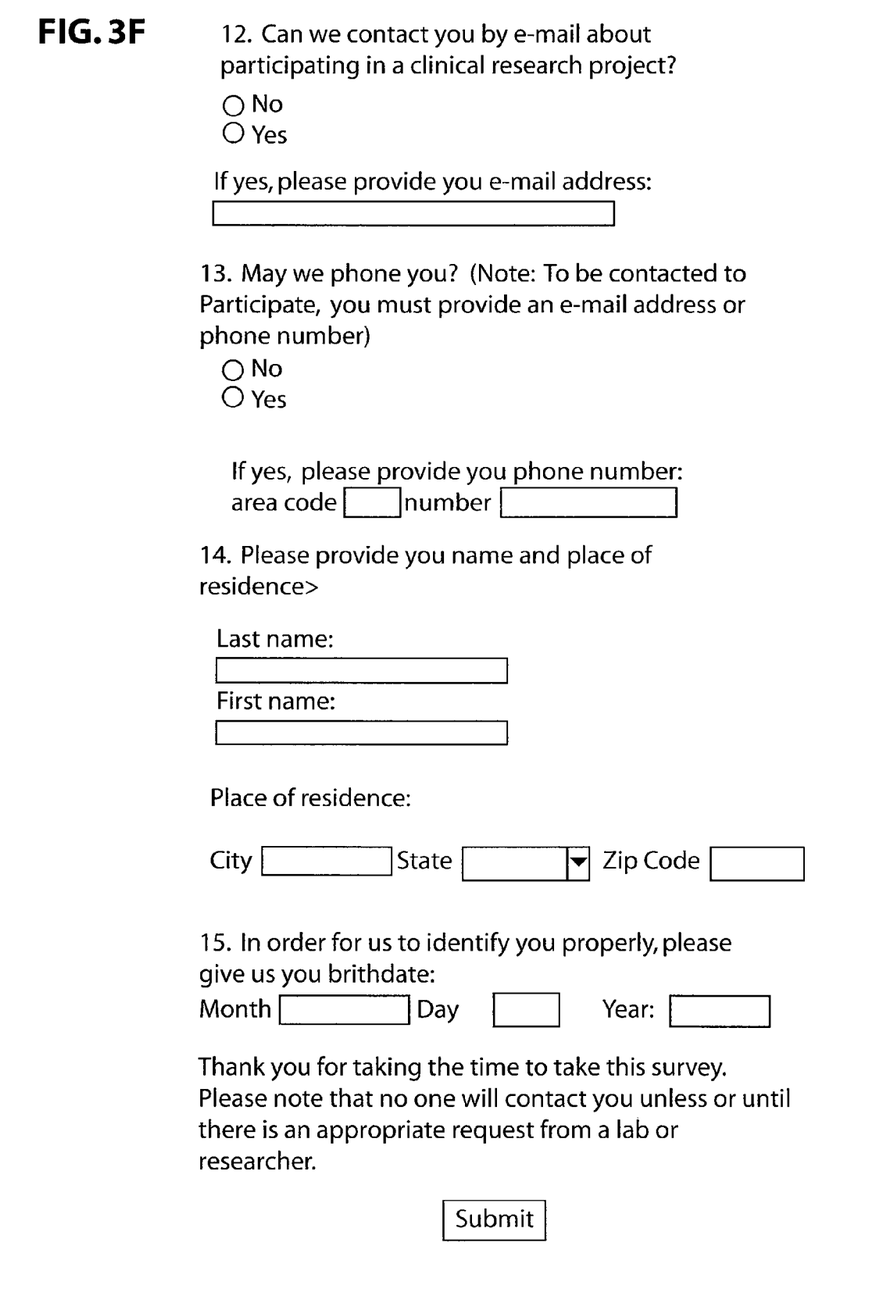

FIG. 2 is an exemplary flow chart of the operation of the secure system for on line recruitment of candidates for clinical trials and research studies. The end user visits the web site and sever 100 automatically generates an introductory home page displayed at the user's computer terminal briefly describing the nature of the services being provided at the web site. In a preferred embodiment, the end user is able to access additional information, e.g., publications, concerning some of the pros and cons associated with participating in a clinical trial, to assist the end user in their decision whether or not to register as a volunteer.

In step 210, server 100, in response to the end user selecting or clicking on a button or icon to proceed or continue, generates a Participation Agreement that is displayed at the end user's computer terminal. The agreement may be drafted, as desired, to cover all legal issues, such as the liabilities and duties of each party. By way of example, the Participation Agreement may include one or more provisions directed to (1) the voluntary nature of the information being provided by the volunteer; (2) the disclaimer of any guarantee of information being provided to clinical researchers or labs; (3) duties on the part of the service to take all reasonable measures to maintain the confidentiality of the data entered by the volunteer; (4) limitations of liability on the part of the service; (5) compensation and ownership rights; (6) independence of the service with respect to the clinical researchers and labs; (7) the volunteer's informed consent upon completing the Health Survey form; (8) authorization by the volunteer to release all data provided in response to the Health Survey form; (9) applicable governing law for disputes which may arise under the contract; and (10) additional provisions directed to laws and regulations in specific states. The end user agrees or consents to be bound by the terms and conditions presented in the Participation Agreement by clicking on an acceptance button or icon before being considered as a possible candidate for a clinical trial or research study.

Upon agreeing or consenting to the terms of the Participation Agreement, for example, by clicking on the acceptance button or icon, in step 220, server 100 produces a Health Survey form display screen at the computer terminal of the end user. FIGS. 3a-3f is an exemplary Health Survey form display screen requesting that the end user enter personal and/or medical information about themselves. By way of example in FIGS. 3a-3f, the end user may be asked personal questions such as their age, sex, name, address, telephone number, and medical questions, such as, their health condition status, how long they have been HIV positive, specific test results, medications the end user is currently taking or has taken in the past, infections or complications the end user may have had or currently has. FIG. 3 also shows some illustrative examples of the type of responses that may be entered by the end user. For example, the end user may be requested to enter text and/or numerical information in a data entry field, select one or more entries from a list of available options, select one or more entries from a pull down menu, or any combination thereof. The Health Survey form may therefore be designed, as desired, depending on such factors as the nature of the particular disease, ailment, disorder or medical condition to which the research studies and clinical trials are directed. Representatives of a registered clinical trial or research study may adapt the questions presented in the Health survey form in accordance with inclusion or exclusion criteria for their particular study.

In FIG. 2, after the end user has responded to all of the questions in the Health Survey form and clicked on a "Submit" button or icon, in step 230, the data entered is automatically encrypted by the volunteer's web browser software before being transmitted to the server 100. Thus, any potential hackers attempting to intercept the confidential information during transmission between the volunteer's computer terminal and the server 100 will be unable to decipher the data.

Thereafter, in step 240 the encrypted data is transmitted from the end user's computer terminal to the server 100 via network 120. In a preferred embodiment, if the end user has not entered a response to one or more questions, then an error message is displayed with the subject matter of the unanswered questions and prompts the end user to go back to the previous screen to correct these responses.

After agreeing to the Consent Agreement and completing the Health Survey form, to confirm that the information provided in response to the Health Survey will be sent directly to the system or server 100, the volunteer may access a digital certificate procured, for example, by Verisign™, to verify communication between the end user's browser and server 100. Alternatively, a digital certificate may be automatically generated in response to the user completing the Health Survey form.

In steps 250-260 of FIG. 2, the encrypted responses to the Health Survey form received at the server 100 are decrypted and stored in memory device 105. The decrypted data stored in memory device 105 is subject to access by potential hackers who gain access to that server to observe the data while in its decipherable state. Server 100 circumvents this potential problem by implementing one or more precautionary measures. In particular, server 100 may be programmed to restrict access to the server to only a minimum number of trusted and screened employees. Security policies and procedures may be implemented to ensure that unauthorized personnel never access the decrypted information received by the server.

In steps 270-280, server 100 processes the volunteer's data responses to the Health Survey, preferably using a specification, such as Common Gateway Interface (CGI) "scripts", to extend the service and capabilities of the web server, and automatically encrypts the processed data using Pretty Good Privacy (PGP) or some other known shareware encryption protocol. Thereafter, in step 290, immediately after encryption, server 100 destroys or purges the unencrypted volunteer's data stored in memory device 105, which, in turn, is replaced with the encrypted processed data. Encrypted processed data stored in memory device 105 is then transmitted from server 100 to the main or central office 110, in step 300.

At the main or central office 110, access to the volunteer's data is restricted to limited personnel. In step 310, the volunteer's data is stored in encrypted form in memory 115. Thereafter, in step 320, the data stored in memory 115 is retrieved and decrypted only when requested by authorized personnel. Encryption keys are preferably stored on an external memory device, such as a floppy disk, a compact disk, or some other storage device, and kept under surveillance, e.g., under lock and key, to which only authorized employees have access.

Figure 4:
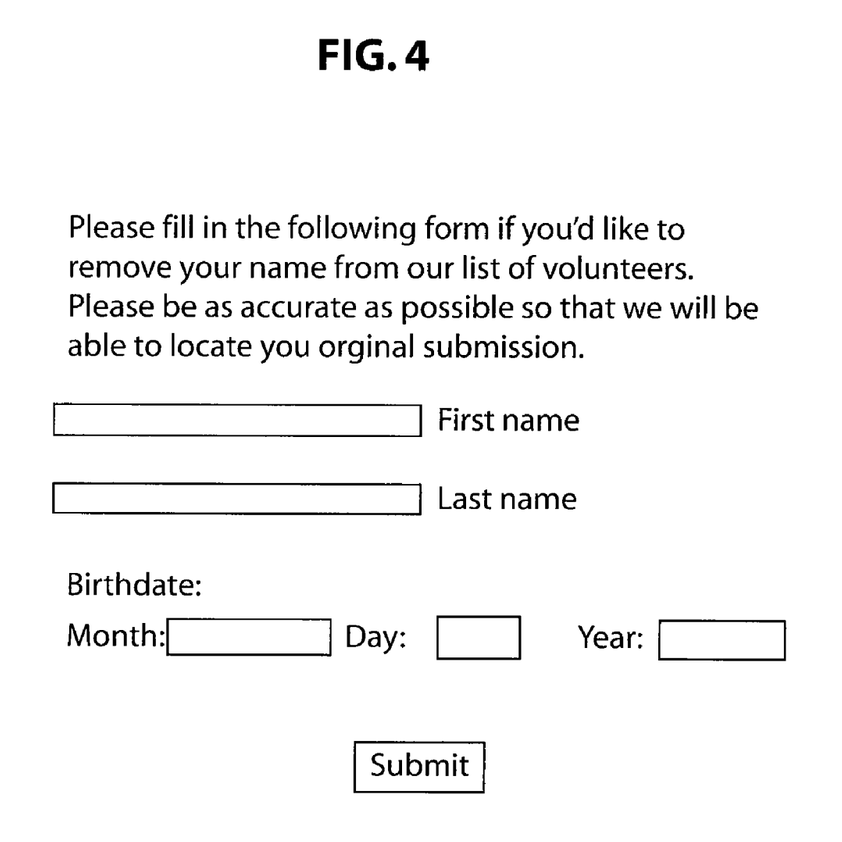
FIG. 4 is an exemplary Opt-out display screen in accordance with the present invention.

At any point in time a volunteer may opt-out by removing their name from the database of volunteers. FIG. 4 is an exemplary Opt-Out form display screen. The volunteer is preferably asked to enter their first name, last name, and date of birth. Any information may be requested so long as the particular volunteer to be removed can be properly identified. Additional information may be used to properly identify the volunteer, such as the maiden name of the volunteer's mother. It is contemplated that the most basic information, e.g., the full name and date of birth of the volunteer, may be initially requested and that additional information will be solicited only if the database identifies multiple matches from the database of volunteers. In an alternative embodiment, the volunteer when registering with the service is assigned a unique identification number that may be subsequently entered by the volunteer when requesting to be removed from the list of potential candidates. In this alternative embodiment, if the volunteer could not recall their identification number, other means for identifying the volunteer as discussed above may be employed.

Researchers and lab technicians interested in accessing the database of volunteers to obtain candidates for its clinical trials and/or research studies register with the central office 110. The registration process may be performed on-line by accessing the web site or via some other communication medium, such as by filling out a printed registration form. By way of example, the registration form may request the name of an authorized officer conducting the research, the subject matter being researched, the medical professionals associated with the research, and the criteria used in the selection of candidates as well as the number of candidates being sought. The completed registration form is forwarded to the central office. In a preferred embodiment of the invention, the central office verifies the credentials and legitimacy of the clinical trial and research study being conducted before establishing an affiliation. Once initial approval is provided, a representative on behalf of the clinical trial or research study must enter into an agreement to be bound by the rules set forth by the central office concerning the prevention against unwanted dissemination of the personal and medical records of its volunteers. A registered clinical researcher or lab may modify the information requested in the Health Survey form based on their own particular needs.

After a volunteer has been selected as a potential candidate for a clinical trial or research study, they are contacted directly by a representative of the clinical trial or research study. All communication is conducted directly between the two parties, without intervention by the central office. In an alternative embodiment, direct contact between a representative on behalf of the clinical trial or research lab and the volunteer is not initiated until the central office first contacts the volunteer and confirms that they still want to be considered as a potential candidate for the particular clinical trial or research study. After confirming that the volunteer stills wishes to be considered as a potential candidate for the particular clinical trial or research study, all communication thereafter would be directly between a representative of the particular clinical trial or research study and the volunteer.

It is desirable to develop a comprehensive security system. Accordingly, additional safeguards are contemplated and within the intended scope of the invention including the use of firewalls or other known security measures. The present invention has been described for recruitment of volunteers as potential candidates for clinical trials or research studies concerning a single disease, e.g., HIV/AIDS. It is, however, contemplated that the server may initially generate a display screen requesting the user to select from a number of diseases, ailments, disorders or medical conditions in which to participate as a volunteer. In this situation the Health Survey form may be modified depending on the particular disease, ailment, disorder or medical condition for which the individual is volunteering.

In the operation of the on-line recruitment system as described above, the volunteer must agree to opt in or opt out of all registered clinical trials or research studies. Alternatively, the system may be adapted so that the server 100 displays a list of all registered clinical trials and research studies that are currently recruiting candidates from which the volunteer may select or target one or more registered clinical researchers/labs that they wish to be listed as a volunteer and be considered as a potential candidate. The volunteer's personal and medical information will only be accessible by those clinical trials and research studies that have been selected by the volunteer.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps which perform substantially the same function, in substantially the same way, to achieve the same results are within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

What is claimed is:

1. A method of on-line recruitment of individuals who want to volunteer with a recruitment service provider for ongoing consideration as potential candidates for participating as research subjects in any of a plurality of clinical trials that register with a recruitment service provider, the method being carried out by means of a server operated by the recruitment service provider, the server being configured to communicate with a plurality of end-user computer terminals via a network, the method comprising the steps of:

provided a participation agreement for display on one of the plurality of end-user computer terminals that is accessible to one of the individuals, the participation agreement soliciting consent from the individual to be considered on an ongoing basis for selection as a potential candidate for participating as a research subject in any of the plurality of clinical trials;

receiving a signal from the one end-user computer terminal indicating the individual's consent to the participation agreement;

providing a health survey form, for display on the one end-user computer terminal, and soliciting contact information and at least one of personal and medical information for the individual from which the individual may be evaluated as a potential candidate for any of the plurality of clinical trials;

receiving information transmitted by the individual via the one of the plurality of end-user computer terminals, the information containing the contact information and at least one of the relevant personal and medical information;

storing the individual's contact information and the at least one of the individual's personal and medical information in a database, thereby registering the individual for consideration as a candidate for participating as a research subject in any of the plurality of clinical trials;

transmitting the stored information to a service provider computer in communication with the server;

receiving an information access request by said recruitment service provider at the computer in communication with the server, said information access request including electronic data to authenticate the identify of said recruitment service provider;

authenticating the identity of said recruitment service provider;

providing access to the individual's retrieved information to said recruitment service provider at the computer of recruitment service provider; and selecting the individual as a potential candidate for one of the plurality of registered clinical trials.

2. The method of claim 1, wherein the participation agreement is a click-wrap agreement.

3. The method of claim 1, wherein the health survey form solicits the identification of one or more medical conditions of the individual relevant to one or more of the plurality of clinical trials.

4. The method of claim 1, wherein the network comprises one or more of the Internet, the World Wide Web, an intranet, a local area network, a wide area network and a wireless communications network.

5. The method of claim 1, further comprising the step of:
transmitting registration information for display on a second end-user computer terminal, said registration information soliciting information for registering a clinical researcher with said recruitment service provider to participate in one or more of the plurality of registered clinical trials.

6. The method of claim 1, wherein the participation agreement signifies consent by the individual to release the contact information to a representative of any one or more of the plurality of clinical trials that may be registered with a recruitment service provider.

7. The method of claim 1, wherein the individual is registered before at least one of the plurality of clinical trials is registered.

8. A method by which individuals may register as volunteers to be considered on an ongoing basis for selection as potential candidates for participating as research subjects in any of a plurality of clinical trials that register with a recruitment service provider, and by which at least one of the individuals may subsequently opt out of the registration, the method being carried out by means of a server operated by the recruitment service provider, the server being configured to communicate with a plurality of end-user computer terminals via a network, the method comprising the steps of:

providing a participation agreement for display on the plurality of end-user computer terminals accessible to the individuals, the participation agreement soliciting consent from each individual to be considered on an ongoing basis for selection as a potential candidate for participating as a research subject in any of the plurality of clinical trials;

receiving signals transmitted by each individual from a respective one of the end-user computer terminals indicating the individual's consent to the participation agreement;

providing a health survey form for display on the respective user computer terminals, the health survey form soliciting from each respective individual contact information by which the individual may be contacted, and at least one of the individual's personal and medical information from which the individual may be evaluated as a potential candidate for any of the plurality of clinical trials;

receiving first information supplied by each individual via the individual's respective end-user computer terminal, the first information containing the individual's contact information, personally-identifying information of the individual and the at least one of the individual's personal and medical information;

storing each individual's contact information, the personally-identifying information of the individual and the at least one of the individual's personal and medical information in a database, thereby registering the individual for ongoing consideration as a potential candidate for participating as a research subject in any of the plurality of clinical trials;

for at least one of the individuals, receiving second information supplied by the at least one individual via one of the plurality of end-user computer terminals, the second information including the personally-identifying information of the at least one individual and information indicating a request by the at least one individual to withdraw the registration;

storing the personally-identifying information of the at least one individual and information indicating the at least one individual's request to withdraw the registration in the database;

transmitting the stored information to a service provider computer in communication with the server;

receiving an information access request by said recruitment service provider at the computer in communication with the server, said information access request including electronic data to authenticate the identify of said recruitment service provider;

authenticating the identity of said recruitment service provider;

providing access to the information to the recruitment service provider at the computer of recruitment service provider; and selecting another one of the individuals other than the withdrawing individual as a potential candidate for one of the plurality of registered clinical trials.

9. The method of claim 8, wherein the personally-identifying information includes a name of the individual in combination with a second personal identifier of the individual.

10. The method of claim 9, wherein the second personal identifier is a date of birth of the individual.

11. The method of claim 8, wherein both the first information and the second information of the at least one withdrawing individual are retrieved from the database in response to the request, further comprising the steps of determining that the personally-identifying information of the second information matches the personally-identifying information of the first information; and withdrawing the registration of the individual.

12. The method of claim 8, wherein the network comprises one or more of the Internet, the World Wide Web, an intranet, a local area network, a wide area network and a wireless communications network.

13. The method of claim 8, wherein the participation agreement is a click-wrap agreement.

14. The method of claim 8, wherein the participation agreement signifies consent by each respective individual to release the contact information of the individual to a representative of any one or more of the plurality of clinical trials that may be registered with a recruitment service provider.

15. The method of claim 8, wherein the health survey form solicits identification of one or more medical conditions of each respective individual relevant to one or more of the plurality of clinical trials that may be registered with a recruitment service provider.

16. The method of claim 8, further comprising the step of:

transmitting registration information for display on a second end-user computer terminal, said registration information soliciting information for e step of a clinical researcher with said recruitment service provider to participate in one or more of the plurality of clinical trials.

17. The method of claim 8, wherein at least one of the individual is registered before at least one of the plurality of clinical trials is registered.

\* \* \* \* \*